United States Patent
Jones

(10) Patent No.: US 10,523,498 B2
(45) Date of Patent: Dec. 31, 2019

(54) MULTI-BROKER MESSAGING AND TELEMEDICINE DATABASE REPLICATION

(71) Applicant: Sierra Nevada Corporation, Sparks, NV (US)

(72) Inventor: David Jones, Sandy, UT (US)

(73) Assignee: SIERRA NEVADA CORPORATION, Sparks, NV (US)

( * ) Notice: Subject to any disclaimer, the term of this patent is extended or adjusted under 35 U.S.C. 154(b) by 166 days.

(21) Appl. No.: 15/650,095

(22) Filed: Jul. 14, 2017

(65) Prior Publication Data
US 2018/0183656 A1    Jun. 28, 2018

Related U.S. Application Data

(60) Provisional application No. 62/438,686, filed on Dec. 23, 2016.

(51) Int. Cl.
*H04L 12/24* (2006.01)
*H04W 84/20* (2009.01)
(Continued)

(52) U.S. Cl.
CPC ...... *H04L 41/0668* (2013.01); *G06F 19/3418* (2013.01); *G16H 10/60* (2018.01); *G16H 40/67* (2018.01); *G16H 80/00* (2018.01); *H04L 41/044* (2013.01); *H04L 41/0816* (2013.01); *H04L 41/30* (2013.01); *H04L 67/1095* (2013.01); *H04W 24/04* (2013.01); *H04W 84/20* (2013.01); *H04L 41/0695* (2013.01); *H04L 43/10* (2013.01); *H04W 24/02* (2013.01)

(58) Field of Classification Search
CPC .............. G06F 19/3418; H04L 41/044; H04L 41/0668; H04L 41/0695; H04L 41/0816; H04L 41/30; H04L 43/10; H04L 67/1095; H04L 12/24; H04W 24/02; H04W 24/04; H04W 84/20; G06H 10/60; G06H 40/67; G06H 80/00
See application file for complete search history.

(56) References Cited

U.S. PATENT DOCUMENTS 5,355,371 A  * 10/1994  Auerbach ............ H04L 12/185
                                                                370/255
5,852,630 A    12/1998  Langberg et al.
(Continued)

FOREIGN PATENT DOCUMENTS

WO    WO-2016/100611 A1    6/2016

OTHER PUBLICATIONS

Agrawal, Amar. "Distributed Algorithms for Mobile Ad Hoc Networks." PowerPoint Presentation. Date last modified Apr. 19, 2005. 20 pages.
(Continued)

*Primary Examiner* — Alina A Boutah
(74) *Attorney, Agent, or Firm* — Mintz Levin Cohn Ferris Glovsky and Popeo, P.C.

(57) ABSTRACT

A master node is provided. The master node can be configured to include multi-broker messaging. The node can be configured to perform Telemedicine Database Replication. A surrogate master node(s) can be provided in a wireless ad-hoc network. In some variations, the master node and surrogate master node(s) can be arranged in a mesh network.

18 Claims, 4 Drawing Sheets

(51) Int. Cl.
*G06F 19/00* (2018.01)
*H04L 29/08* (2006.01)
*H04W 24/04* (2009.01)
*G16H 80/00* (2018.01)
*G16H 40/67* (2018.01)
*G16H 10/60* (2018.01)
*H04W 24/02* (2009.01)
*H04L 12/26* (2006.01)

(56) References Cited

U.S. PATENT DOCUMENTS

| | | | |
|---|---|---|---|
| 6,072,795 A | 6/2000 | Poulter | |
| 6,115,830 A * | 9/2000 | Zabarsky | G06F 11/1482 707/999.002 |
| 6,195,687 B1 * | 2/2001 | Greaves | G09B 5/14 345/504 |
| 6,363,416 B1 * | 3/2002 | Naeimi | H04L 12/66 709/209 |
| 6,638,218 B2 | 10/2003 | Bulat | |
| 6,757,898 B1 | 6/2004 | Ilsen et al. | |
| 6,801,943 B1 | 10/2004 | Pavan et al. | |
| 6,839,541 B2 | 1/2005 | Alzoubi et al. | |
| 6,889,338 B2 * | 5/2005 | Srinivasan | H04L 1/22 714/13 |
| 6,993,587 B1 * | 1/2006 | Basani | H04L 67/1095 709/229 |
| 7,011,629 B2 | 3/2006 | Bulat | |
| 7,058,367 B1 | 6/2006 | Luo et al. | |
| 7,264,590 B2 | 9/2007 | Casey et al. | |
| 7,333,528 B1 | 2/2008 | Miao | |
| 7,387,607 B2 | 6/2008 | Holt et al. | |
| 7,421,578 B1 * | 9/2008 | Huang | H04L 63/065 370/254 |
| 7,430,608 B2 | 9/2008 | Noonan et al. | |
| 7,436,801 B1 | 10/2008 | Kanterakis | |
| 7,451,221 B2 | 11/2008 | Basani et al. | |
| 7,461,130 B1 * | 12/2008 | AbdelAziz | H04W 84/20 709/208 |
| 7,532,585 B2 * | 5/2009 | Kim | H04L 29/06 370/254 |
| 7,587,465 B1 | 9/2009 | Muchow | |
| 7,590,550 B2 | 9/2009 | Schoenberg | |
| 7,649,872 B2 | 1/2010 | Naghian et al. | |
| 7,691,059 B2 | 4/2010 | Bulat | |
| 7,801,030 B1 * | 9/2010 | Aggarwal | H04L 12/44 370/227 |
| 7,970,633 B2 | 6/2011 | Bulat | |
| 7,974,924 B2 | 7/2011 | Holla et al. | |
| 8,126,728 B2 | 2/2012 | Dicks et al. | |
| 8,126,729 B2 | 2/2012 | Dicks et al. | |
| 8,126,730 B2 | 2/2012 | Dicks et al. | |
| 8,131,564 B2 | 3/2012 | Dicks et al. | |
| 8,131,565 B2 | 3/2012 | Dicks et al. | |
| 8,131,566 B2 | 3/2012 | Dicks et al. | |
| 8,140,356 B2 | 3/2012 | Dicks et al. | |
| 8,155,982 B2 | 4/2012 | Dicks et al. | |
| 8,214,489 B2 | 7/2012 | Ballette et al. | |
| 8,225,015 B2 | 7/2012 | Gao-Saari et al. | |
| 8,255,238 B2 | 8/2012 | Powell et al. | |
| 8,260,709 B2 | 9/2012 | Holla et al. | |
| 8,310,336 B2 | 11/2012 | Muhsin et al. | |
| 8,380,631 B2 | 2/2013 | Dala et al. | |
| 8,396,801 B1 | 3/2013 | Dala et al. | |
| 8,396,802 B2 | 3/2013 | Dala et al. | |
| 8,396,803 B1 | 3/2013 | Dala et al. | |
| 8,396,804 B1 | 3/2013 | Dala et al. | |
| 8,549,142 B2 | 10/2013 | Goose et al. | |
| 8,583,958 B2 * | 11/2013 | Surkov | H04L 67/1051 714/4.1 |
| 8,792,384 B2 | 7/2014 | Banerjee et al. | |
| 8,908,537 B2 | 12/2014 | Fedyk et al. | |
| 8,942,228 B1 | 1/2015 | Chen et al. | |
| 9,031,070 B2 | 5/2015 | Mentze et al. | |
| 9,391,805 B2 | 7/2016 | Wang et al. | |
| 2003/0129993 A1 | 7/2003 | Overy et al. | |
| 2003/0148767 A1 | 8/2003 | Sugaya et al. | |
| 2003/0204625 A1 * | 10/2003 | Cain | H04L 45/00 709/243 |
| 2004/0233972 A1 | 11/2004 | Karaoguz | |
| 2005/0094574 A1 * | 5/2005 | Han | H04L 29/06 370/254 |
| 2005/0132154 A1 * | 6/2005 | Rao | H04L 67/1097 711/162 |
| 2005/0190818 A1 | 9/2005 | Sunaga et al. | |
| 2005/0276255 A1 | 12/2005 | Aiello et al. | |
| 2006/0125356 A1 | 6/2006 | Meek et al. | |
| 2006/0221856 A1 * | 10/2006 | Quiroz | H04W 84/20 370/254 |
| 2006/0240777 A1 | 10/2006 | Ruuska | |
| 2006/0253557 A1 * | 11/2006 | Talayco | H04L 41/0806 709/220 |
| 2007/0152837 A1 | 7/2007 | Bischoff et al. | |
| 2007/0213600 A1 | 9/2007 | John et al. | |
| 2007/0230594 A1 | 10/2007 | Mo et al. | |
| 2008/0052127 A1 | 2/2008 | Rosenfeld et al. | |
| 2008/0065416 A1 | 3/2008 | Mazar et al. | |
| 2008/0086658 A1 | 4/2008 | Takahasi | |
| 2008/0088437 A1 | 4/2008 | Aninye et al. | |
| 2008/0144493 A1 | 6/2008 | Yeh | |
| 2008/0288646 A1 * | 11/2008 | Hasha | H04L 67/1095 709/228 |
| 2009/0088607 A1 | 4/2009 | Muraca | |
| 2009/0257475 A1 | 10/2009 | Haque et al. | |
| 2009/0292555 A1 | 11/2009 | Brown | |
| 2010/0142409 A1 * | 6/2010 | Fallon | H04L 41/0206 370/255 |
| 2010/0318699 A1 | 12/2010 | Gao-Saari et al. | |
| 2010/0329317 A1 | 12/2010 | Tzannes | |
| 2011/0051906 A1 | 3/2011 | Cioffi et al. | |
| 2011/0081858 A1 | 4/2011 | Tolentino et al. | |
| 2011/0196965 A1 | 8/2011 | Romero et al. | |
| 2012/0047133 A1 * | 2/2012 | Wang | G06F 16/958 707/726 |
| 2012/0124412 A1 * | 5/2012 | Surkov | H04L 67/1051 714/4.2 |
| 2012/0173281 A1 | 7/2012 | DiLella et al. | |
| 2013/0170499 A1 * | 7/2013 | Ramanujan | H04W 40/26 370/401 |
| 2013/0191688 A1 * | 7/2013 | Agarwal | H04L 41/0873 714/32 |
| 2013/0218588 A1 * | 8/2013 | Kehr | A61B 5/4839 705/2 |
| 2014/0181027 A1 | 6/2014 | Whitehead et al. | |
| 2014/0210616 A1 * | 7/2014 | Ramachandran | G08B 21/0227 340/539.13 |
| 2014/0298091 A1 * | 10/2014 | Carlen | H04L 65/80 714/15 |
| 2014/0301431 A1 | 10/2014 | Nair et al. | |
| 2014/0303994 A1 * | 10/2014 | Johnson | G06F 19/3418 705/2 |
| 2014/0330582 A1 | 11/2014 | Tong et al. | |
| 2014/0330584 A1 | 11/2014 | Pillers et al. | |
| 2015/0033295 A1 * | 1/2015 | Huster | G06F 21/44 726/4 |
| 2015/0319226 A1 | 11/2015 | Mahmood | |
| 2016/0037386 A1 | 2/2016 | Pitchaiah et al. | |
| 2016/0156502 A1 * | 6/2016 | Fugitt | H04L 41/30 709/205 |
| 2016/0380778 A1 * | 12/2016 | Shen | H04W 40/00 709/209 |
| 2017/0027436 A1 | 2/2017 | Lee et al. | |
| 2017/0063731 A1 * | 3/2017 | Muller | H04L 69/325 |
| 2017/0063965 A1 * | 3/2017 | Grenader | G06F 9/4881 |
| 2017/0116289 A1 * | 4/2017 | Deshmukh | G06F 16/24535 |
| 2017/0126603 A1 * | 5/2017 | Chen | H04L 51/14 |
| 2017/0222877 A1 * | 8/2017 | Sagot | H04W 40/24 |
| 2018/0004908 A1 | 1/2018 | Barrus et al. | |
| 2018/0034904 A1 * | 2/2018 | Roy | H04L 67/1034 |
| 2018/0054219 A1 | 2/2018 | Qian et al. | |
| 2018/0059754 A1 * | 3/2018 | Shaikh | G06F 1/30 |
| 2018/0091588 A1 * | 3/2018 | Qin | H04L 67/1012 |

(56) References Cited

U.S. PATENT DOCUMENTS

| | | | |
|---|---|---|---|
| 2018/0097845 A1* | 4/2018 | Chen | H04L 41/12 |
| 2018/0262401 A1* | 9/2018 | Shah | H04W 4/38 |
| 2018/0331940 A1* | 11/2018 | Jadhav | H04L 45/121 |

OTHER PUBLICATIONS

Al Shayeji, Mohammad, et. al. "Analysis and Enhancements of Leader Elections Algorithms in Mobile Ad Hoc Networks." *ACEEE International Journal of Network Security* vol. 2, No. 4, (2011), 5 pages.

Chandra, Ranveer, et. al. "Anonymous Gossip: Improving Multicast Reliability in Mobile Ad-Hoc Networks." *21st International Conference on Distributed Computing Systems*, (2001), Mesa, AZ. pp. 275-283.

Chung, Hyun, et. al. "Optimal Regional Consecutive Leader Election in Mobile Ad-Hoc Networks." *2011 Proceedings of the 7th ACM SIGACT/SIGMOBILE International Workshop on Foundations of Mobile Computing*, New York, NY. (2011), pp. 52-61.

Comstock, Jonah. "American Well sues Teladoc for alleged patent infringement." Mobilehealthnews.com. Jun. 8, 2015. Web. Retrieved Jun. 29, 2015. 2 pages. Source URL: http://mobihealthnews.com/44163/american-well-sues-teladoc-for-alleged-patent-infringement/.

Jayapal, Cynthia and Sumathi Vembu. "Adaptive Service Discovery Protocol for Mobile Ad Hoc Networks." *European Journal of Scientific Research*, vol. 49, No. 1, (2011), pp. 6-17.

Malpani, Navneet, et. al. "Leader Election Algorithms for Mobile Ad Hoc Networks." *2000 Proceedings of the 4th International Workshop on Discrete Algorithms and Methods for Mobile Computing and Communications*. (2000), pp. 96-103.

Melit, Leila and Nadjib Badache. "A Highly Adaptive Leader Election Algorithm for Mobile Ad Hoc Networks." *International Conference on Advanced Aspects of Software Engineering ICAASE*, Nov. 2-4, 2014, Constantine, Algeria. (2014), pp. 181-184.

Singh, Anu, et. al. "A Process Calculus for Mobile Ad Hoc Networks." *Science of Computer Programming*, vol. 75 No. 6, (2010), pp. 440-469.

Toner, Stephen and Donal O'Mahony. "Self-Organising Node Address Management in Ad-hoc Networks." *Personal Wireless Communications*, (2003), Lecture Notes in Computer Science, vol. 2775., pp. 476-483.

Vasudevan, Sudarshan, et. al. "Secure Leader Election in Wireless Ad Hoc Networks" Umass Computer Science Technical Report 01-50, (2001). 31 pages.

Vasudevan, Sudarshan, et. al. "Design and Analysis of a Leader Election Algorithm for Mobile Ad Hoc Networks." *2004 Proceedings of the 12th IEEE International Conference on Network Protocols*, Washington, DC. (2004), pp. 350-360.

\* cited by examiner

MULTI-BROKER MESSAGING AND TELEMEDICINE DATABASE REPLICATION

CROSS-REFERENCE TO RELATED APPLICATIONS

This application claims priority to and the benefit of U.S. Provisional Patent Application No. 62/438,686, titled "Master Node With Multi-Broker Messaging and Telemedicine Database Replication," filed on Dec. 23, 2016, the disclosure of which is incorporated herein by reference in its entirety.

TECHNICAL FIELD

The subject matter described herein relates to maintaining the wireless transmission of data over a wireless network and telemedicine database replication.

BACKGROUND

In communication networks, if the central message broker fails or is unavailable, other network nodes within a network cannot communicate. When the network has a telemedicine application patient care devices, that are nodes of the network, cannot transmit patient data. Similarly, a user device of a medical provider cannot obtain patient data, status information, or the like.

SUMMARY

In one aspect a method can be provided. The method can include one or more of the following operations. An election message can be transmitted. The election message can be transmitted by a network node and in response to a failure to connect to a master network node. The transmitting can use a message broker of the network node. The network node can be at least part of a network. One or more other election messages can be received at the network node. The one or more other election messages can be received from one or more other network nodes. A network hierarchy of the network node can be compared with one or more other network hierarchies of the one or more other network nodes. The network node can be designated as another master node. The designating of the network node as the master node can be in response to the network hierarchy of the network node being superior to the one or more other network hierarchies of the one or more other network nodes. An instruction can be transmitted to the one or more other network nodes. The instruction can be to use the message broker of the network node for communicating over the network.

The network node being the another master node can be configured to at least control communication over the network. The network node being the another master node can be a hub node and the one or more other network nodes can be spoke nodes. The network can be an ultra-wideband network. The network can be a wireless ad-hoc network. The network node can be a user device. The network can comprises one or more patient care devices configured to at least obtain patient data from a patient.

The patient data can be received at the network node being the another master node and stored at the network node and in a patient data database. A copy of at least a portion of the patient data database can be transmitted from the network node to one or more of the one or more other network nodes.

The network can comprise a subnetwork comprising a plurality of subnetwork network nodes. The network can comprise a surrogate master node configured to at least be a message broker for the plurality of subnetwork network nodes. The surrogate master node can be configured to at least communicate with the network node using the message broker of the network node.

A master node can be provided. The master node can be configured to include multi-broker messaging. The node can be configured to perform Telemedicine Database Replication. A surrogate master node(s) can be provided in a wireless ad-hoc network. In some variations, the master node and surrogate master node(s) can be arranged in a mesh network.

Implementations of the current subject matter can include, but are not limited to, methods consistent with the descriptions provided herein as well as articles that comprise a tangibly embodied machine-readable medium operable to cause one or more machines (e.g., computers, etc.) to result in operations implementing one or more of the described features. Similarly, computer systems are also described that may include one or more processors and one or more memories coupled to the one or more processors. A memory, which can include a computer-readable storage medium, may include, encode, store, or the like one or more programs that cause one or more processors to perform one or more of the operations described herein. Computer implemented methods consistent with one or more implementations of the current subject matter can be implemented by one or more data processors residing in a single computing system or multiple computing systems. Such multiple computing systems can be connected and can exchange data and/or commands or other instructions or the like via one or more connections, including but not limited to a connection over a network (e.g. the Internet, a wireless wide area network, a local area network, a wide area network, a wired network, or the like), via a direct connection between one or more of the multiple computing systems, etc.

The details of one or more variations of the subject matter described herein are set forth in the accompanying drawings and the description below. Other features and advantages of the subject matter described herein will be apparent from the description and drawings, and from the claims. While certain features of the currently disclosed subject matter are described for illustrative purposes in relation to a telemedicine system, it should be readily understood that such features are not intended to be limiting. The claims that follow this disclosure are intended to define the scope of the protected subject matter.

DESCRIPTION OF DRAWINGS

The accompanying drawings, which are incorporated in and constitute a part of this specification, show certain aspects of the subject matter disclosed herein and, together with the description, help explain some of the principles associated with the disclosed implementations. In the drawings.

DETAILED DESCRIPTION

A wireless network can comprise a plurality of network nodes. One network node of the plurality of network nodes can be designated as a master node. The master node can be configured to manage communications of the plurality of network nodes. The master node can be configured to include multi-broker messaging. In some examples, a plurality of network nodes can be configured to obtain patient data of one or more patients. In such networks, the master node can be configured to perform telemedicine database replication. In some examples, one or more of the plurality of network nodes may be out of range of the master node. In such situations, a surrogate master node(s) can be designated. Each surrogate master node can form a wireless ad-hoc network for a subset of the plurality of network nodes. In some variations, the master node and/or surrogate master node(s) can be arranged in a mesh network.

In distributed networking, efficiency can be achieved by arranging nodes in a hub-spoke network. In a hub-spoke network, a master node can be selected that serves as the hub for messaging and data distribution for the network. One or more other nodes can be in electronic communication directly with the master node, each of the one or more other nodes can be a spoke in the hub-spoke network architecture. In some examples, the presently described hub-spoke architecture can reduce the number of required network paths. For example, data intended for a particular node, of a hub-spoke network, can be transmitted, by the master node, directly to that particular node, rather than requiring the data to be relayed by one or more other nodes and/or broadcast to all nodes within a network. In some variations, the master node can be configured to serve as the message broker for communication between one or more of the hub node and/or the other nodes.

Having the master node configured to serve as the message broker can be problematic for ad-hoc wireless networks where the master node may not always be available to all other network nodes. For example, the master node may be out of range of one or more of the other nodes. Signals may be blocked between the transmitting node and the master node. In some examples, when the master node is unavailable to one or more of the spoke nodes, a different available node can be elected to act as the master node. In some examples, the newly elected master node may function as a surrogate master node. A surrogate master node can function as a master node to one or more other nodes that are out of range, or are incapable of communicating with a master node. The surrogate node itself, can be a spoke node of the master node and in communication with the master node.

Figure 1:
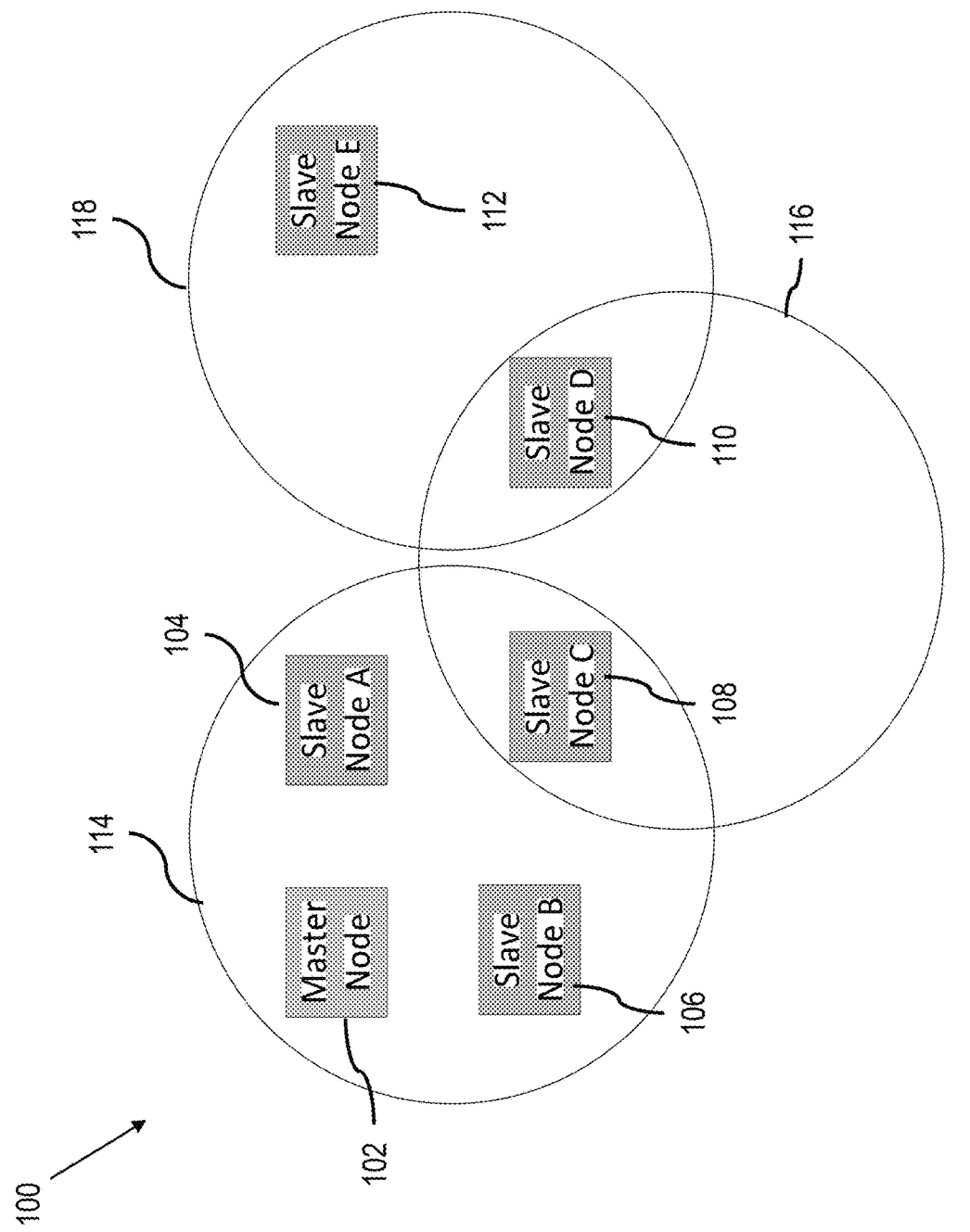
FIG. 1 is a schematic illustration of a distributed network having master nodes and slave nodes, in accordance with one or more aspects of the presently described subject matter.

FIG. 1 is a schematic illustration of a distributed network 100 having one or more features consistent with the presently described subject matter. The network 100 can have a master node 102. The network 100 can have one or more slave nodes 104-112. As stated above, in a distributed network, such as network 100, communication efficiency can be achieved by designating a node as a master node, such as master node 102. The master node 102 can serve as a hub for messaging and data distribution for one or more slave nodes that are within communication range of the master node 102. In some implementations, a slave node can serve as a hub for messaging and data distribution for one or more network nodes that are outside the range of the master node 102. In some implementations, a slave node may serve as a hub for messaging and data distribution for a subnetwork. A subnetwork can comprise of one or more network nodes having a common master node. When a slave node, for example, slave node 108 acts as a master node for a subnetwork, for example, subnetwork 116, that slave node can be referred to as a surrogate master node for that subnetwork. In the example illustrated in FIG. 1, slave node 108 is a surrogate master node for subnetwork 116. Slave node 108 being in range of master node 102 allows the slave node 108 to relay messages and/or data between the master node 102 and another slave node that is out of range of the master node 102, but within range of the slave node 108. In the example, illustrated in FIG. 1, such a node can be slave node 110.

A subnetwork can include a master node that is a hub, one or more slave nodes, forming the spokes of a hub and spoke network. The master node for a subnetwork can itself be a slave node to another node, rendering that node a surrogate master node. For example, subnetwork 114 comprises a master node 102 and multiple slave nodes 104-108. The communication lines between the master node 102 and slave node(s) 104-108 function as spokes to the hub.

In some examples, one or more nodes of a network may be out of range of the master node 102. In implementations consistent with FIG. 1, slave node 110 and slave node 112 are out of range of the master node 102. However, there are some slave nodes that are within both the range of the master node 102 and within the range of the slave node 110. In such examples, a slave node within range of a master node as well as being within range of one or more network nodes that are outside of the range of the master node can become a surrogate master node for those out-of-range network nodes. In the example illustrated in FIG. 1, slave node 108 is within range of master node 102 and is also within range of slave node 110. The slave node 108 and the slave node 110 form a subnetwork 116. The slave node 108 can be configured to act as a surrogate master node for subnetwork 116, which includes the slave node 110.

Similarly, as shown in FIG. 1, slave node 112 is out of range of the master node 102 and slave node 108 (which is the surrogate master node of the subnetwork 116). However, slave node 112 is within the range of slave node 110. Slave node 110 can become the surrogate master node for the slave node 112 and also for the subnetwork 118. The number of nodes in each subnetwork 114, 116 and 118, can have an arbitrary number of network nodes. The number of network nodes in any given subnetwork can be dependent on the range of the master node and/or surrogate master node for that given subnetwork, the processing capabilities of the master node and/or surrogate master node in the given subnetwork, the number of communication channels of the master node and/or surrogate master node, or the like.

Master node 102 can have a master node message broker that can be used as the message broker for all messages communicated over the network 100. In some examples, each node in a network can be configured to serve as a message broker. In some examples, a node can be selected as the master node for an entire network. Similarly, a node can be selected as a master node for a subnetwork, the subnetwork being a subset of the network. The master node for the subnetwork can be referred to as a surrogate master node and configured to relay messages and data between the master node for the network and one or more nodes within the subnetwork. In some variations, the surrogate master node can have a separate message broker for the subnetwork compared to the message broker used by the master node for the network. This can reduce interference between different subnetworks and/or different surrogate master nodes and the master node for the network.

In some variations, one node can be selected as the message broker for the network and/or subnetwork. This node can be referred to as the master node. Every other node in a network, that isn't currently serving as the message broker, can subscribe to the messages from the message broker provided by the master node. In some examples, the nodes within a network can elect a master node to serve as the active message broker using a standard master node election algorithm, for example, the bully algorithm. All other message brokers within a cluster can become dormant until there is a need for another master node election. A similar technique can be used for each node within a subnetwork of network nodes. A subnetwork of network nodes can use standard master node election algorithms to select a master node for that cluster. A master node for a subnetwork can be referred to as a surrogate master node. In some examples, the surrogate master node can be a slave node to a master node for the network, communicating with the master node using a first message broker. The surrogate master node can further communicate with slave nodes within the subnetwork using a second message broker.

In one non-limiting implementation, the process described herein for multi-broker messaging can be applied to telemedicine. For example, biological sensors can be provided. One or more computing devices can be configured to communicate with each other wirelessly to manage the health care of several patients, say, using database replication between computing network nodes. Database replication between computing network nodes can include replicating a database on a first node onto one or more second nodes. A centralized server may also have a wireless connection to gather and store information about the patient care across the wireless network.

Figure 2A:
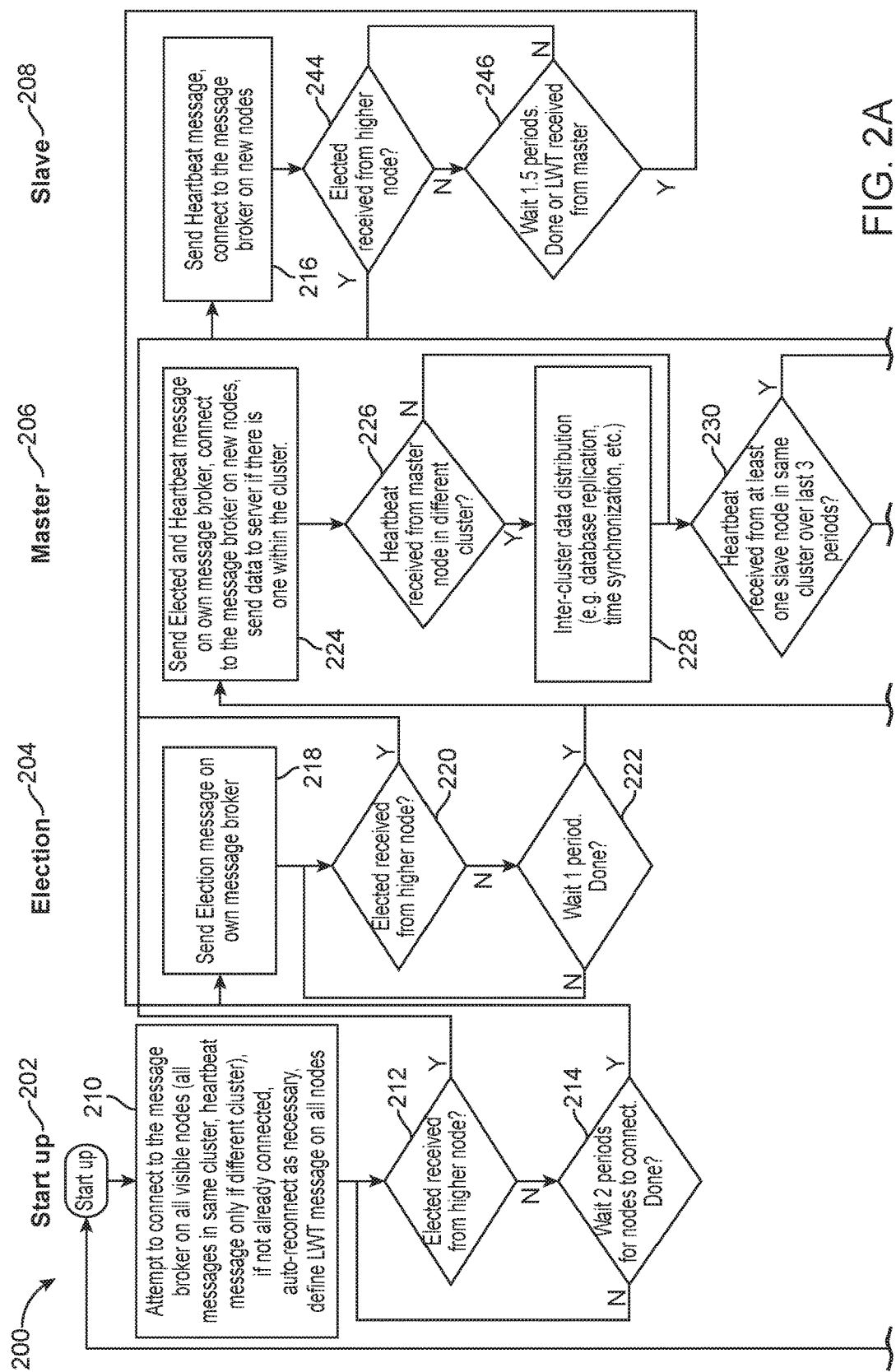
FIGS. 2A-2B show a process flow diagram illustrating aspects of a method having one or more features consistent with implementations of the current subject matter.
Figure 2B:
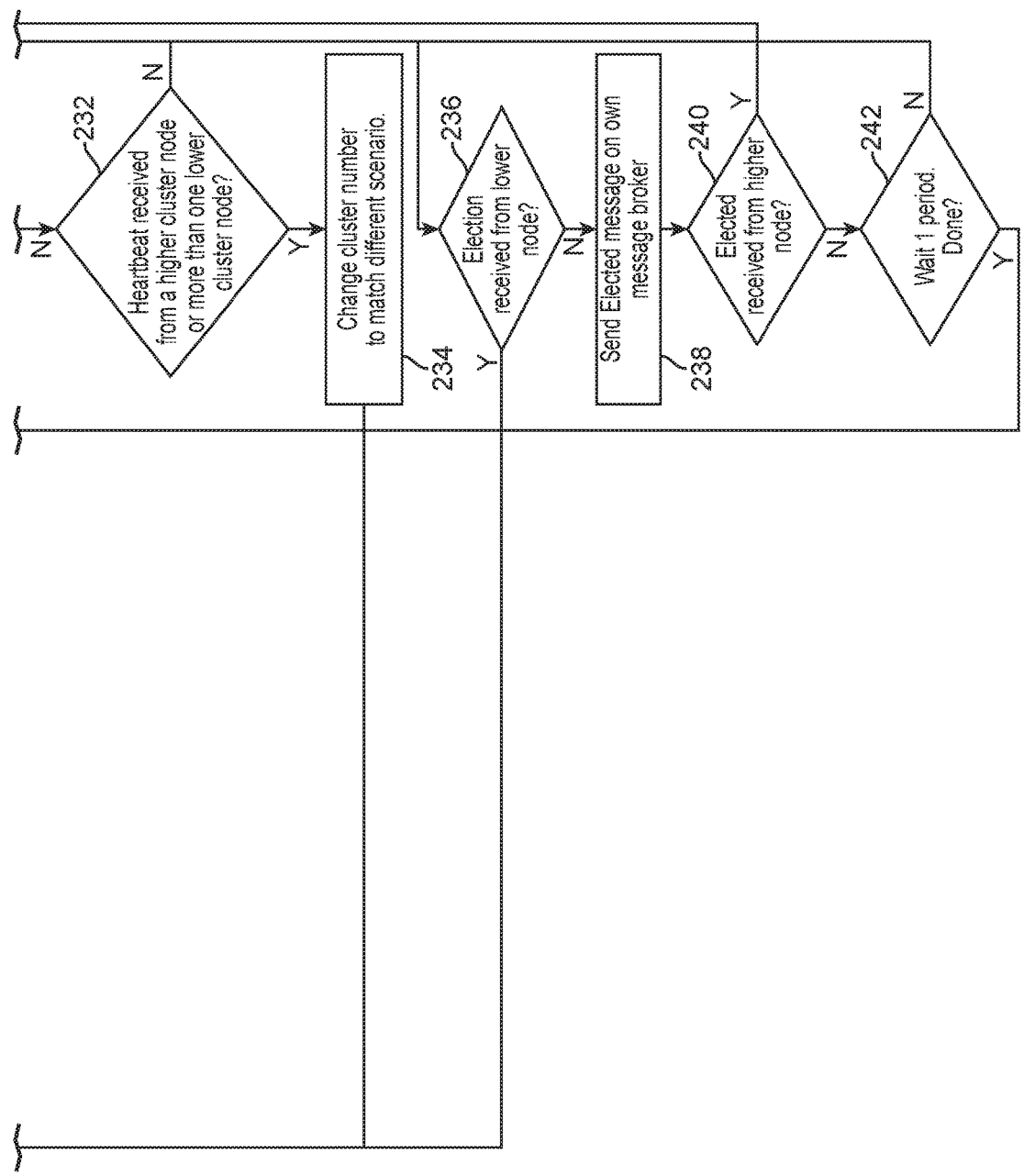

FIGS. 2A-2B show a process flow diagram illustrating aspects of a method 200 having one or more features consistent with the presently described subject matter. One or more operations of the method 200 can be performed by a network node. The network node, for example, can be a network node such as those illustrated in FIG. 1. In FIGS. 2A-2B, the network node can be configured to obtain heartbeat information associated with a patient. In some implementations, method 200 can include the transmission of multiple messages for a network node in different states, a startup state 202, an election state 204, a master state 206 and a slave state 208.

When in the election state 204, the network node can be configured to transmit an election message using its own message broker. The election message can initiate the election of a master node for the network, subnetwork and/or network cluster. A network cluster can include a master node and one or more slave nodes. In some implementations the network cluster can include one or more surrogate master nodes. The one or more surrogate master nodes can be in addition to the master node and the one or more slave nodes. The one or more surrogate master nodes may be the one or more slave nodes, being slave nodes to the master node.

If an elected message is received within a predetermined time period, at the network node and from a network node having a higher hierarchical level, then the network node, that received the elected message from the network node having the higher hierarchical level, can transition to the slave state 208. Alternatively, if no elected message is received from a network node having a hierarchical level, the network node can be configured to broadcast an elected message on its own message broker and can transition to a master state 206.

When in the master state 206, after the election has been made when in the election state 204, a message can be sent by the newly elected master node using the master node's message broker. The master node can be configured to broadcast, using the master node's message broker, the status of the master node. Data from one or more network nodes connected, or subscribed, to the master node can be transmitted to the master node using the master node's message broker. A network node in a master state 206 can be referred to herein as a master node.

When in a master state 206, the network node can be configured to perform one or more master tasks. Master tasks can include, for example, updating a server, managing inter-cluster communication with master nodes of other network clusters, transitioning subscription to a different network cluster, handling election messages from network nodes having a lower hierarchical level, or the like. In response to an elected message being received at the network node in a master state 206 and from a network node having a higher hierarchical level, the network node in the master state 206 can transition to a slave mode 208.

In the event of a determination that a connection break between the master node and one or more network nodes, the message broker can be configured to transmit a last will and testament (LWT) message. The LWT message can be configured to notify all network nodes that subscribe to the master node, that there is a connection break.

When a network node is in a startup state 202, the message broker subscription process can be initiated. The LWT message, that will be used in the event of a connection break, can be defined. The network node can wait to determine whether it received an election message from an existing master node or a network node having a higher hierarchical level. If an existing master node received an election message from another network node that has a higher hierarchical level than that existing master node, the existing master node can transition into a slave state 208, and subscribe to the new master node. When the network node is in a slave state, the network node can be referred to herein as a slave node.

When the network node is in a slave state 208, the slave node can use the master node as a hub for distributing data with other nodes that are part of the same network and/or network cluster as the slave node. For example, the slave node can use the master node for database synchronization between other network nodes and other network clusters. The master node can be configured to serve as a reference for time synchronization between the nodes of a network cluster served by the master node. For example, if the slave node receives a LWT message from the master node, or if the master node fails to send out periodic elected messages, then the slave node can transition to the election mode 204.

When a slave node becomes a surrogate master node a set of surrogate messages can be used. The surrogate messages can be broadcast using the message broker of the surrogate master node. For example, a surrogate message can broadcast the priority of the master node on the surrogate master node's message broker. The surrogate messages can be ignored by slave nodes that are within direct range of the master node. However, the surrogate messages can override the election messages for slave nodes that are outside of the direct range of the master node, or outside of the cell served by the master node. For example, with reference to FIG. 1, the surrogate messages can cause slave node 110 to have slave node 108 as the surrogate master node for slave node 110. A surrogate message can provide time synchronization to slave node 110. In such a situation, for example, bidirectional database replication can happen between slave node 108 and slave node 110. A similar situation can occur between slave node 110 and slave node 112. In some variations, there may be a limit to the number layers of surrogate master nodes. The limit of the number of layers of surrogate master nodes may be predicated on performance limits, or the like.

With reference to FIGS. 2A-2B, the method 200 provides an example of the transitions between the various states of a network node.

At 210, when a network node initializes, the network node can attempt to connect to a message broker on all visible nodes. The connecting can be as part of an automatic re-connect.

At 212, a determination can be made as to whether a network node having a higher hierarchical level has been elected as the master node. At 214, in response to a determination that no node having a hierarchical level has been elected as the master node, the network node can wait a predetermined period of time to connect to a master network node.

At 216, in response to connecting to a master network node, the network node can be configured to be a slave node. In some variations, the network node itself can be configured to select a mode of the network node. When connected to a master node, the network node can be configured to modify a mode of the network node so that the network node can enter a slave node mode. In the slave node mode, the network node, configured to obtain heartbeat data, can send the heartbeat data to the master node. The network node can be configured to send the heartbeat data using the master node's message broker.

In response to a determination, at 214, that the network node has not connected to a master node, the network node can be configured to determine whether an election of a node, as the master node, has been received.

The network node can enter an election mode 204. In an election mode 204, the network node, at 218, can be configured to send an election message, using the message broker of the network node, to one or more other network nodes within the network, or network cluster.

At 220, the network node can be configured to determine whether an election message has been received from one or more other network nodes having a higher hierarchical level compared to the network node.

At 222, in response to a determination that no other network node having a higher hierarchical level has transmitted an election message, the network node can be configured to wait a predetermined period of time for receipt of an election message from another network node having a higher hierarchical level.

In response to determining, at 222, that no election message from another network node having a higher hierarchical level, had been received, the network node can enter a master mode 106. The network node can be configured to modify its own mode into the master mode.

At 224, the network node can be configured to transmit the heartbeat data and the notification that it is the master node. The notification that the network node is the master node can be transmitted using the message broker of the network node. The notification can be transmitted to all other network nodes in range of the network node. In some variations, the heartbeat information can be transmitted, using the message broker of the network node, to the master node of a different network cluster.

At 226, a determination can be made as to whether information has been received from a master node of a different network cluster.

At 228, in response to a determination that information has been received from the master node of the different network cluster, data from the network node can be distributed to one or more other master nodes of other network clusters. The distribution of the data can include database replication, time synchronization, or the like.

At 230, a determination can be made if a network heartbeat has been received at the network node from one or more slave nodes within the network cluster of the network node. The network node can be configured to wait a predetermined period of time to receive the network heartbeat. A network heartbeat can be a message from the slave node to a master node indicating that the slave node is still functioning and connected to the network.

At 232, in response to a determination that no network heartbeat has been received at the network node from one or more slave nodes within the network cluster, a determination can be made as to whether a network heartbeat has been received from a node of a network cluster having a higher hierarchical level compared to the network cluster of the network node.

At 234, in response to determining that a network heartbeat has been received, at the network node, from a network node of a network cluster having a higher hierarchical level, the network node can be configured to change its network cluster number. A network cluster number can be an indication of a hierarchical level of the network cluster compared to one or more other network clusters.

At 236, in response to no network heartbeat being received, at operation 232, from a higher cluster node or more than one lower cluster node, a determination can be made as to whether an election message has been received from a node having a lower hierarchical level.

At 238, in response to a determination, at operation 236, that no election message has been received from another node, the network node can be configured to transmit an election message to the one or more other nodes of the network and/or network cluster. The transmission of the election message can be sent using the message broker of the network node.

At 240, the network node can be configured to determine whether an election message has been received from a network node having a higher hierarchical level. In response to a determination that an election message has been received from a network node having higher hierarchical level, the network node can be configured to enter a slave mode 208. The network node can be configured to transmit messages using the message broker of the network node having the higher hierarchical level.

At 242, in response to a determination that no election message has been received from a node having a higher hierarchical level, the network node can be configured to wait for a predetermined period of time. In response to no other election message being received from another network node, the network node can be configured to perform the operations at 224.

At 244, the network node is in a slave mode 208. When in a slave mode, at 244, the network node can be configured to determine whether an election message has been received from a network node having a higher hierarchical level. In response to a determination that the network node has received a message from a higher hierarchical level, the network node can maintain the slave mode 208. In some variations, the network node may be connected to a first master node. The first master node being another network node having a hierarchical level higher than the network node. The network node may lose the connection with the first master node. The network node may receive an election message from a second master node. The second master node being a different network node having a hierarchical level higher than the network node. In such circumstances, the network node can be configured to use the second master node message broker to communicate data rather than the first master node message broker.

At 246, in response to determining that no election message has been received from a network node having a higher hierarchical level, the network node can wait a predetermined period of time before it transmits, at 218, its own election message on its own message broker.

In one non-limiting example, a product utilizing the method 200 described with respect to FIGS. 2A-2B, can include a telemedicine application that requires the efficient communication of information between different nodes without interruption. In response to a master node handling communication of telemedicine data becoming unavailable, one or more slave nodes can become the master nodes and/or a surrogate master node allowing the telemedicine communication system to continue functioning.

In some implementations consistent with the present description, a master node, when used in telemedicine, can be a medical military module. The medical military module can be connected to a user device platform. The user device platform can include one or more of a tablet, a laptop, another computing device, or the like. In some variations, the user device can provide the computing power to determine the interference estimation within the ultra-wideband network. In some examples, one or more slave nodes connected to a medical military module with the user device platform can include patient care device modules connected to patient care devices (PCDs). The patent care device modules and medical military modules can be configured to communicate over an ultra-wideband network. The medical military module(s) and the patient care device module(s) can be configured to estimate an amount of the level of interference at their location and communicate the amount of estimated interference level back to the master node, which can be a master medical military module having a user device.

Patient care devices can be configured to monitor patients and/or gather patient data. For example, the one or more patient care devices 808-814 can be configured to monitor an oxygen level, a heartrate, a heartbeat pattern, a temperature, a respiration rate, a blood pressure, or the like. The patient care devices and/or patient care device modules can be configured to transmit the patient data to the user devices and/or medical military modules.

The network used for telemedicine applications can include an ultra-wideband network. The network nodes can be configured to communicate using ultra-wideband communication channels.

Figure 3:
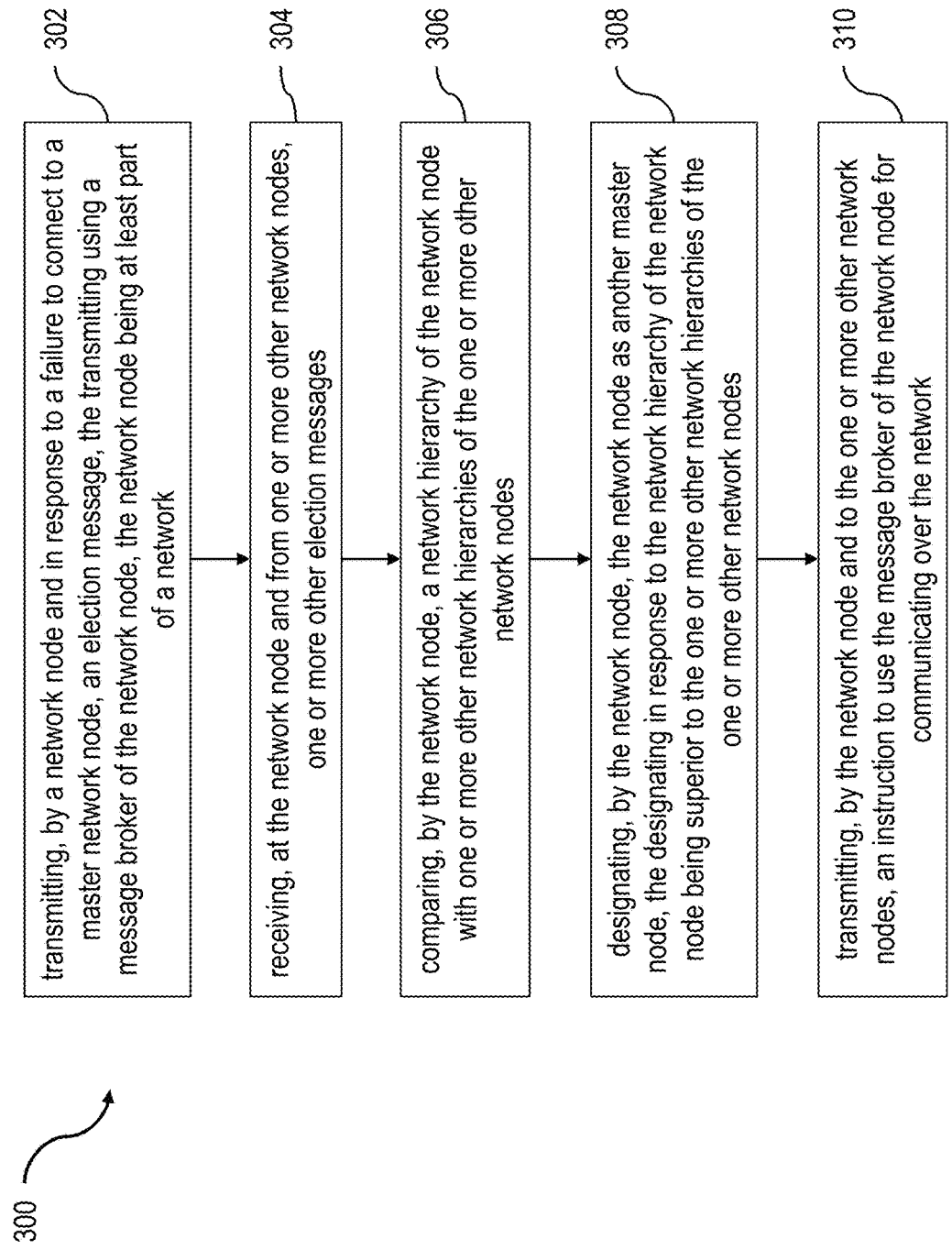
FIG. 3 is a process flow diagram illustrating aspects of a method having one or more features consistent with implementations of the current subject matter.

FIG. 3 is an illustration of a process flow of a method 300 having one or more features consistent with the presently described subject matter.

At 302, an election message can be transmitted. The election message can be transmitted by a network node. The election message can be transmitted in response to a failure to connect to a master network node. The election message can be transmitted using a message broker of the network node.

At 304, one or more other election messages can be received at the network node. The one or more other election messages can be received from one or more other network nodes. The one or more other network nodes can be within the network and/or network cluster.

At 306, a network hierarchy of the network node can be compared with one or more other network hierarchies of the one or more other network nodes. In some examples, a hierarchy level of a network node can be set arbitrarily. In some examples, a hierarchy level of a network node can be set based on one or more performance parameters of the network node. For example, a network node may have capability to handle communications from multiple network nodes and pass those communications on to other network nodes, a server, or the like. In some examples, the hierarchy of a network node can be dependent on an address of the network node, such as an IP address of the network node. A network node may have multiple receivers, transmitters and/or transceivers, configured to communicate on multiple different channels, bandwidths, air interfaces, or the like. Other network nodes may have the capability of transmitting and receiving data from one other network node only.

At 308, the network node can designate the network node as another master node. The designating can be in response to the network hierarchy of the network node being superior to the one or more other network hierarchies of the one or more other network nodes.

At 310, the network node can transmit, to the one or more other network nodes, an instruction to use the message broker of the network node for communicating over the network. In such a manner, the network node can become the master node for the network and/or network cluster.

When the network node is the another master node, the network node can control and/or manage the communication on the network and/or network cluster. The network node as the another master node can be a hub in a hub-spoke network architecture. The other network nodes can be spokes in a hub-spoke network architecture.

In some variations, the network and/or network cluster can be an ultra-wideband network, a wireless ad-hoc network, or the like.

The network node can be a user device having a telemedicine application. The other network nodes can include patient care devices having a telemedicine application. The patient care devices can be configured to monitor patients and/or collect patient data. The user device can be configured to receive the patient data, update a patient data database, transmit the patient data to a server, present the patient data on a screen associated with the user device, or the like.

In some variations, the network node as the master network node can be configured to facilitate replication of the patient data database. For example, the network node as the master network node can be configured to transmit, to at least one of the one or more other network nodes, a copy of at least a portion of the patient database.

In one non-limiting example, an advantage of the presently described subject matter is to overcome a situation where a messaging server goes offline preventing all network nodes from communication with each other. The presently described subject matter facilitates the continued communication between network nodes of a network cluster in the event that a master node, of that network cluster, becomes unavailable for communication. The master node ordinarily managing the communications between the network nodes of its associated network cluster.

One or more of the features described herein can be performed by one or more processors. The processor(s) can be configured to provide information processing capabilities to one or more computing devices having one or more features consistent with the current subject matter. The computing device(s) can be, for example, a smart device, a telephone, a computer, or the like. Processor(s) may include one or more of a digital processor, an analog processor, a digital circuit designed to process information, an analog circuit designed to process information, a state machine, and/or other mechanisms for electronically processing information. Processors can be a single entity, multiple entities, collocated, or located in separate buildings. In some implementations, the processor(s) can include a plurality of processing units. These processing units can be physically located within the same device, or processor and may represent processing functionality of a plurality of devices operating in coordination. The processor can be configured to execute machine-readable instructions, which, when executed by the processor(s) may cause the processor(s) to perform one or more of the functions described in the present description. The functions described herein may be executed by software; hardware; firmware; some combination of software, hardware, and/or firmware; and/or other mechanisms for configuring processing capabilities on the processor(s).

The processor(s) can be disposed in each of the nodes and one or more of the processors can be configured to perform the various features described herein. The processor(s) can be configured to execute machine-readable instructions stored on electronic storage media. The machine-readable instructions, when executed by the processor(s), can cause the processor(s) to perform one or more of the functions described herein. In some variations, one processor disposed at one node may perform a first set of functions and a different processor disposed at a different node may perform a second set of functions.

One or more aspects or features of the subject matter described herein can be realized in digital electronic circuitry, integrated circuitry, specially designed application specific integrated circuits (ASICs), field programmable gate arrays (FPGAs) computer hardware, firmware, software, and/or combinations thereof. These various aspects or features can include implementation in one or more computer programs that are executable and/or interpretable on a programmable system including at least one programmable processor, which can be special or general purpose, coupled to receive data and instructions from, and to transmit data and instructions to, a storage system, at least one input device, and at least one output device. The programmable system or computing system may include clients and servers. A client and server are generally remote from each other and typically interact through a communication network. The relationship of client and server arises by virtue of computer programs running on the respective computers and having a client-server relationship to each other.

These computer programs, which can also be referred to programs, software, software applications, applications, components, or code, include machine instructions for a programmable processor, and can be implemented in a high-level procedural language, an object-oriented programming language, a functional programming language, a logical programming language, and/or in assembly/machine language. As used herein, the term "machine-readable medium" refers to any computer program product, apparatus and/or device, such as for example magnetic discs, optical disks, memory, and Programmable Logic Devices (PLDs), used to provide machine instructions and/or data to a programmable processor, including a machine-readable medium that receives machine instructions as a machine-readable signal. The term "machine-readable signal" refers to any signal used to provide machine instructions and/or data to a programmable processor. The machine-readable medium can store such machine instructions non-transitorily, such as for example as would a non-transient solid-state memory or a magnetic hard drive or any equivalent storage medium. The machine-readable medium can alternatively or additionally store such machine instructions in a transient manner, such as for example as would a processor cache or other random access memory associated with one or more physical processor cores.

To provide for interaction with a user, one or more aspects or features of the subject matter described herein can be implemented on a computer having a display device, such as for example a cathode ray tube (CRT) or a liquid crystal display (LCD) or a light emitting diode (LED) monitor for displaying information to the user and a keyboard and a pointing device, such as for example a mouse or a trackball, by which the user may provide input to the computer. Other kinds of devices can be used to provide for interaction with a user as well. For example, feedback provided to the user can be any form of sensory feedback, such as for example visual feedback, auditory feedback, or tactile feedback; and input from the user may be received in any form, including, but not limited to, acoustic, speech, or tactile input. Other possible input devices include, but are not limited to, touch screens or other touch-sensitive devices such as single or multi-point resistive or capacitive trackpads, voice recognition hardware and software, optical scanners, optical pointers, digital image capture devices and associated interpretation software, and the like.

In the descriptions above and in the claims, phrases such as "at least one of" or "one or more of" may occur followed by a conjunctive list of elements or features. The term "and/or" may also occur in a list of two or more elements or features. Unless otherwise implicitly or explicitly contradicted by the context in which it used, such a phrase is intended to mean any of the listed elements or features individually or any of the recited elements or features in combination with any of the other recited elements or features. For example, the phrases "at least one of A and B;" "one or more of A and B;" and "A and/or B" are each intended to mean "A alone, B alone, or A and B together." A similar interpretation is also intended for lists including three or more items. For example, the phrases "at least one of A, B, and C;" "one or more of A, B, and C;" and "A, B, and/or C" are each intended to mean "A alone, B alone, C alone, A and B together, A and C together, B and C together, or A and B and C together." Use of the term "based on," above and in the claims is intended to mean, "based at least in part on," such that an unrecited feature or element is also permissible.

The subject matter described herein can be embodied in systems, apparatus, methods, and/or articles depending on the desired configuration. The implementations set forth in the foregoing description do not represent all implementations consistent with the subject matter described herein. Instead, they are merely some examples consistent with aspects related to the described subject matter. Although a few variations have been described in detail above, other modifications or additions are possible. In particular, further features and/or variations can be provided in addition to those set forth herein. For example, the implementations described above can be directed to various combinations and subcombinations of the disclosed features and/or combinations and subcombinations of several further features disclosed above. In addition, the logic flows depicted in the accompanying figures and/or described herein do not necessarily require the particular order shown, or sequential order, to achieve desirable results. Other implementations may be within the scope of the following claims.

What is claimed is:

1. A method, comprising:
transmitting, by a first network node, a first election message, the first election message being transmitted in response to the first network node failing to connect to a second network node serving as a master network node of a subnetwork including the first network node and the second network node, the transmitting using a message broker of the first network node, the second network node being a slave node to a third network node serving as a master network node to a network including the subnetwork;
receiving, at the first network node and from a fourth network node in the subnetwork, a second election message;
comparing, by the first network node, a network hierarchy level of the first network node with a network hierarchy level of the fourth network node;
designating, by the first network node, the first network node as the master network node of the subnetwork based at least on the network hierarchy level of the first network node being higher than the network hierarchy level of the fourth network node, the first network node becoming another slave node of the third network node as a result of the designating; and
transmitting, by the first network node and to the fourth network node, an instruction to use the message broker of the first network node for communicating over the network.

2. The method of claim 1, wherein the first network node designated as the master network node of the subnetwork is configured to at least control communication between the fourth network node and the third network node.

3. The method of claim 1, wherein the first network node designated as the master network node of the subnetwork becomes a hub node of the subnetwork with the fourth network node being a spoke node of the subnetwork.

4. The method of claim 1, wherein the network is an ultra-wideband network.

5. The method of claim 1, wherein the network is a wireless ad-hoc network.

6. The method of claim 1, wherein the first network node, the second network node, the third network node, and/or the fourth network node comprise one or more user devices.

7. The method of claim 1, wherein the first network node, the second network node, the third network node, and/or the fourth network node comprises one or more patient care devices configured to at least obtain patient data from a patient.

8. The method of claim 7, further comprising:
receiving, at the first network node designated as the master node, patient data obtained at the fourth network node; and
storing, at the first network node and in a patient data database, the patient data.

9. The method of claim 7, further comprising:
transmitting, by the first network node designated as the master network node, at least a portion of the patient data to a fifth network node outside of the subnetwork by at least transmitting the portion of the patient data to the third network node.

10. A system comprising:
a processor; and,
a memory storing machine-readable instructions, which when executed by the processor, cause the processor to perform one or more operations comprising:
transmitting, by a first network node, a first election message, the first election message being transmitted in response to the first network node failing to connect to a second network node serving as a master network node of a subnetwork including the first network node and the second network node, the transmitting using a message broker of the first network node, the second network node being a slave node to a third network node serving as a master node to a network including the subnetwork;
receiving, at the first network node and from a fourth network node in the subnetwork, a second election message;
comparing, by the first network node, a network hierarchy level of the first network node with a network hierarchy level of the fourth network node;
designating, by the first network node, the first network node as the master node of the subnetwork based at least on the network hierarchy level of the first network node being higher than the network hierarchy level of the fourth network node, the first network node becoming another slave node of the third network node as a result of the designating; and
transmitting, by the first network node and to the fourth network node, an instruction to use the message broker of the first network node for communicating over the network.

11. The system of claim 10, wherein the first network node designated as the master node of the subnetwork is configured to at least control communication between the fourth network node and the third network node.

12. The system of claim 10, wherein the first network node designated as the master node of the subnetwork becomes a hub node of the subnetwork with the fourth network node being a spoke node of the subnetwork.

13. The system of claim 10, wherein the network is an ultra-wideband network.

14. The system of claim 10, wherein the network is a wireless ad-hoc network.

15. The system of claim 10, wherein the first network node, the second network node, the third network node, and/or the fourth network node comprise one or more user devices.

16. The system of claim 10, wherein the first network node, the second network node, the third network node, and/or the fourth network node comprises one or more patient care devices configured to at least obtain patient data from a patient.

17. The system of claim 16, wherein the one or more operations further comprise:
receiving, at the first network node designated as the master node, patient data obtained at the fourth network node; and
storing, at the first network node and/or in a patient data database, the patient data.

18. The system of claim 16, wherein the one or more operations further comprise:
transmitting, by the first network node designated as the master network node, at least a portion of the patient data to a fifth network node outside of the subnetwork by at least transmitting the portion of the patient data to the third network node.

\* \* \* \* \*